(12) United States Patent
Choi (10) Patent No.: US 6,847,234 B2
(45) Date of Patent: Jan. 25, 2005

(54) COMPARISON APPARATUS OPERATED AT A LOW VOLTAGE

(75) Inventor: Soo-Chang Choi, Ichon-shi (KR)

(73) Assignee: Hynix Semiconductor Inc., Kyoungki-do (KR)

( * ) Notice: Subject to any disclaimer, the term of this patent is extended or adjusted under 35 U.S.C. 154(b) by 0 days.

(21) Appl. No.: 10/617,832

(22) Filed: Jul. 14, 2003

(65) Prior Publication Data

US 2004/0108879 A1 Jun. 10, 2004

(30) Foreign Application Priority Data

Oct. 31, 2002 (KR) .................................. 10-2002-0067125

(51) Int. Cl.[7] .............................................. H03K 5/22
(52) U.S. Cl. ........................... 327/65; 327/89; 341/156; 341/159
(58) Field of Search .............................. 327/64, 52, 57, 327/58, 62, 63, 65, 77–82, 89; 341/156, 159

(56) References Cited

U.S. PATENT DOCUMENTS

| | | | |
|---|---|---|---|
| 4,749,955 A | 6/1988 | Cook | 330/253 |
| 5,397,936 A | 3/1995 | Wang | 327/77 |
| 5,416,484 A | 5/1995 | Lofstrom | 341/159 |
| 5,498,982 A | * 3/1996 | Gopinathan et al. | 326/126 |
| 5,563,598 A | 10/1996 | Hickling | 341/155 |
| 6,459,306 B1 | 10/2002 | Fischer et al. | 327/67 |
| 6,597,303 B2 | * 7/2003 | Cosand | 341/165 |
| 2004/0027265 A1 | * 2/2004 | Michalski | |

* cited by examiner

Primary Examiner—Tuan T. Lam
(74) Attorney, Agent, or Firm—Birch, Stewart, Kolasch & Birch, LLP (57) ABSTRACT

The present invention provide an CMOS comparator outputting one bit digital signal after comparing two analog input signals through alternately performing a track mode operation and latch mode operation decided by a clock signal having a constant period, including: a latching unit having the main/sub input terminal; a first switching transistor having the clock signal as a gate input and having one end coupled to main input terminal; a first load transistor diode-connected to the other end of the first switching transistor and a ground end; a second switching transistor having a gate receiving the clock signal as a gate input and one end coupled to the sub input terminal; and a second load transistor diode-connected to the second switching transistor and to the other end of the ground terminal.

7 Claims, 8 Drawing Sheets

COMPARISON APPARATUS OPERATED AT A LOW VOLTAGE

FIELD OF THE INVENTION

The present invention relates to a comparison apparatus; and, more particularly, to the same operated at a high speed and at a low voltage by using an analog signal.

DESCRIPTION OF RELATED ARTS

Recently, complementary metal oxide semiconductor (CMOS) process techniques are common. Accordingly, a system on chip (SOC) technique integrating a number of circuits on one chip became important to a modern industry. The SOC is integrated with an analog circuit processing an analog signal as well as a large scale digital circuit capable of performing a complicated logic operation. A process technique for large scale integration less than 0.18 µm can be used for a transistor device operated at a low voltage less than 1.8 Voltage (V). A conventional circuit design may be applied to the digital circuit. However, in this case, it is not possible to apply it to an analog circuit because an operation range of the transistor is substantially limited at such low voltage. Accordingly, a new circuit design should be required.

An analog to digital converter (ADC) among a number of analog circuits integrated at the SOC is a most important block capable of controlling whole SOC.

Concisely describing a conversion principal of the ADC, an analog input signal is first compared with a finely subdivided standard voltage and converted to a digital value. Consequently, the ADC is used to convert an analog type of input signal to a digital type of output signal.

The ADC is used for a peripheral device of a communication circuit, a digital signal processor (DSP), and a microcontroller unit (MCU). In addition, the ADC is broadly used for all kinds of circuit chips requiring an interface of the analog signal and the digital signal.

Usually, the ADC uses a 2-phase clocked comparator operated by a clock signal and such comparator could have two operation types classified by the clock signal, that is, a track mode and a latch mode. In a first mode, that is, the track mode, two input analog signals are tracked by being amplified to have a low gain. In a second phase, that is, the latch mode, the amplified signal is applied to a positive feedback circuit. Continuously, a polarity of the signal is latched and thereafter, outputting one bit digital signal.

Figure 1:
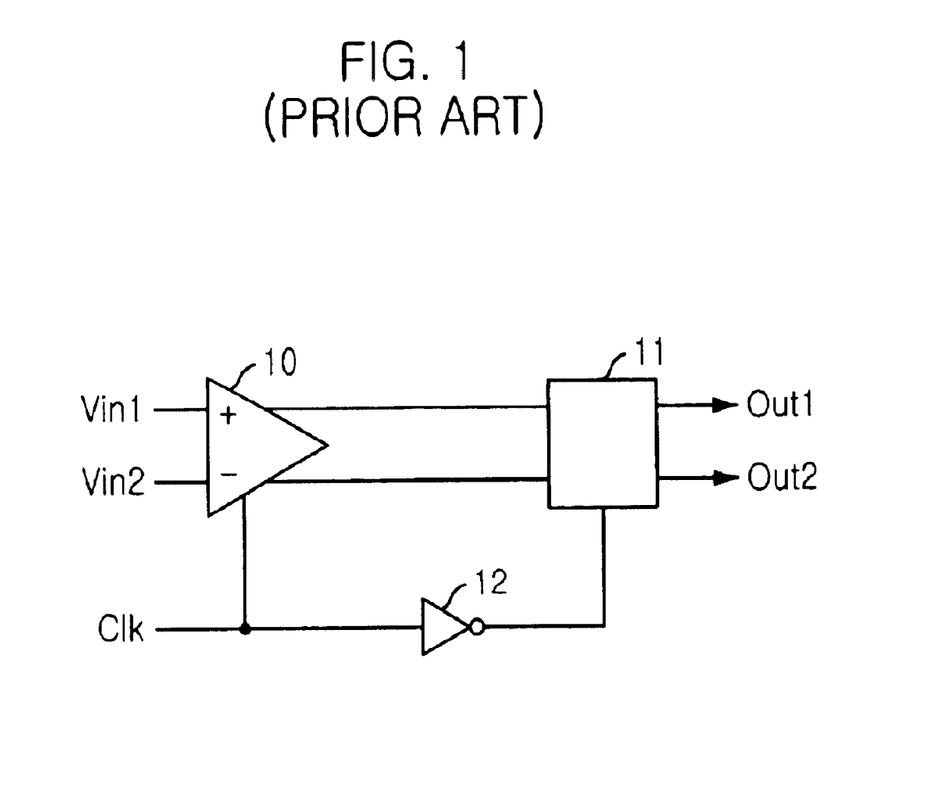
FIG. 1 is a block diagram showing a constitution of a CMOS comparator used for a common ADC.

FIG. 1 is a block diagram showing a constitution of a CMOS comparator used for a conventional ADC. Herein, the CMOS comparator is constituted with an amplification unit 10 and a latch circuit 11. Herein, the amplification unit amplifies a difference of a standard signal and an input signal, and the latch circuit latches the difference. An amplifier used for the CMOS comparator mentioned above does not need to be a linear or a closed loop, and obtains a virtually infinite gain by forming a positive feedback of the latch circuit.

Figure 2:
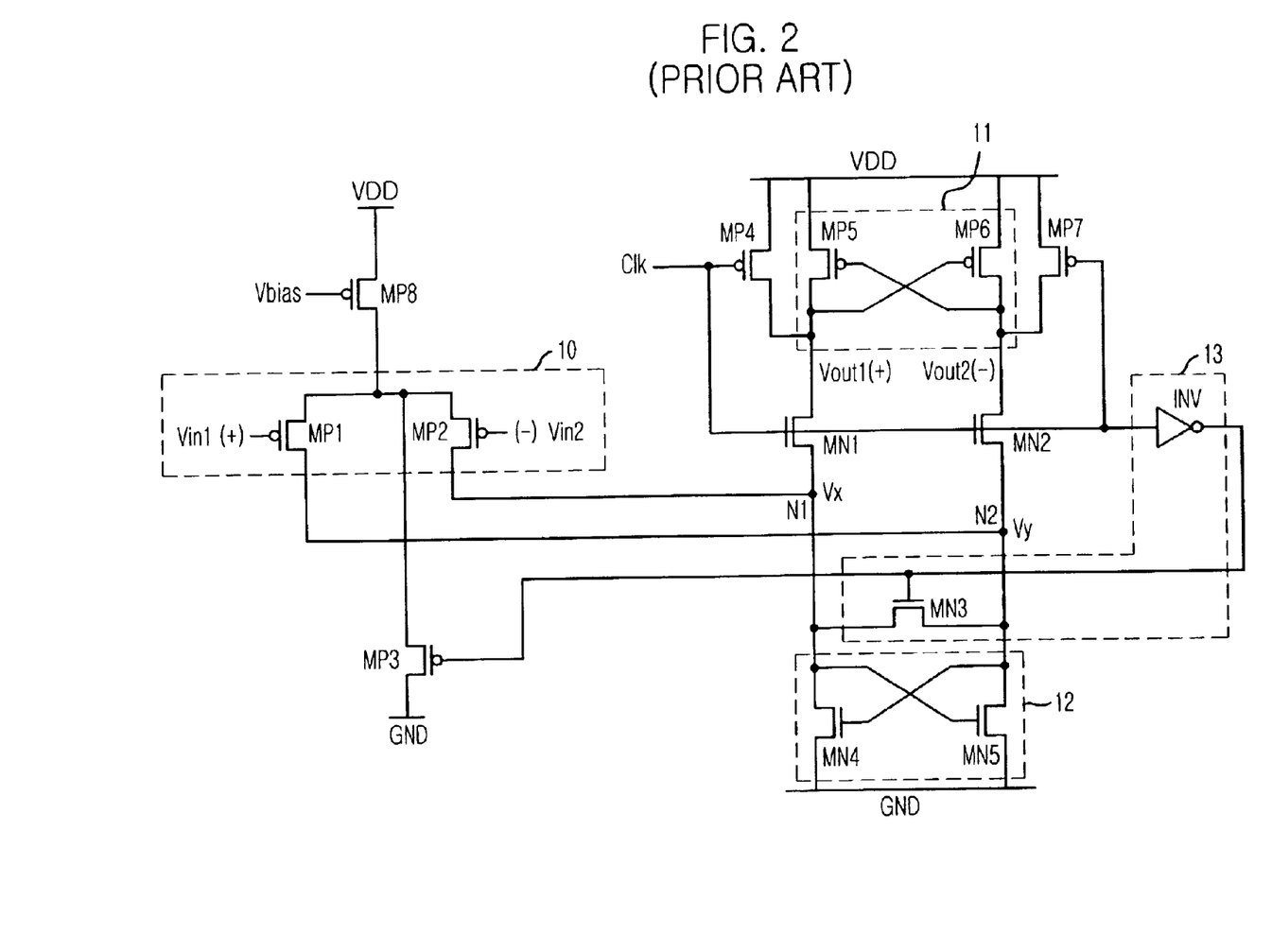
FIG. 2 is a circuit diagram of the CMOS comparator shown in FIG. 1 more precisely.

FIG. 2 is a circuit diagram specifically illustrating the comparator shown in FIG. 1 (Ref. "Principles of data conversion system design—Behzad Razavi (AT&T Bell Laboratories)" IEEE PRESS 189p.)

As shown, the comparator device is constituted with a differential pair input unit 10 constituted with a first PMOS transistor MP1 and a second PMOS transistor MP2, a first latching unit 11 constituted with a fifth PMOS transistor MP5 and a sixth transistor MP6. Herein, both gates of the fifth and the sixth PMOS transistors are cross-coupled to two output terminals Vout1 and Vout2 respectively, a second latching unit 12 constituted with a fourth NMOS transistor and a fifth NMOS transistor, wherein both gates of the fourth and the fifth NMOS transistors MN4 and MN5 are cross-coupled to a first node and a second node respectively, an inverter, a third NMOS transistor MN3 controlling the clock signal which can operate the second latching unit 12 in the track mode or the latch mode, Herein, the third NMOS transistor MN3 is formed between the first node N1 and the second node N2 corresponding to both drains of the fourth and the fifth NMOS transistor MN4 and MN5. A clock signal Clk inverted by the inverter INV is applied to the followings: a gate of the third NMOS transistor MN3 and making the second latching unit 12 serve as the amplifier having a constant turn-on resistance during a track mode operation; a coupled fourth PMOS transistor MP4 and a first NMOS transistor MP4; and another coupled seventh PMOS transistor MP7 and second NMOS transistor MN2 which get alternately turned on and off by the clock signal Clk, a third PMOS transistor MP3 being turned on during a latch mode operation and serving as a source follower turning off the differential pair input unit 10 by forming a current pass from a drain voltage terminal VDD to a ground terminal GND, and a bias transistor MP8.

Figure 3:
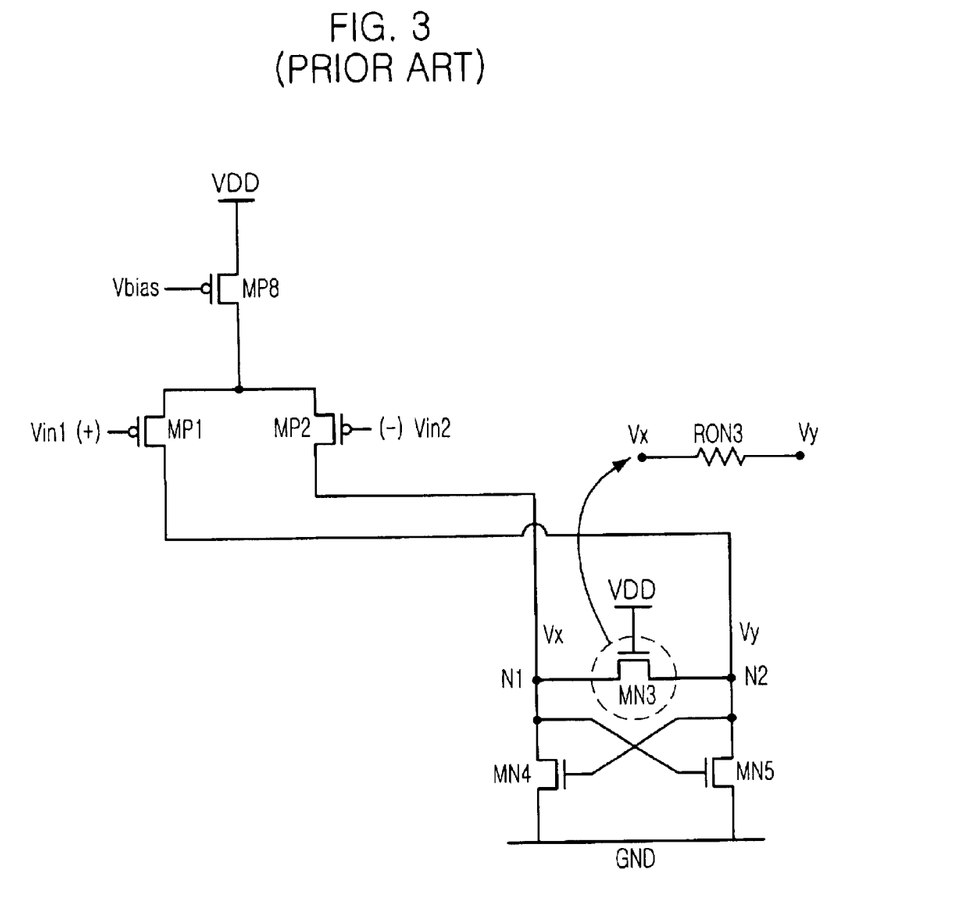
FIG. 3 is an equivalent circuit diagram of the comparator operated in a track mode as shown in FIG. 2.
Figure 4:
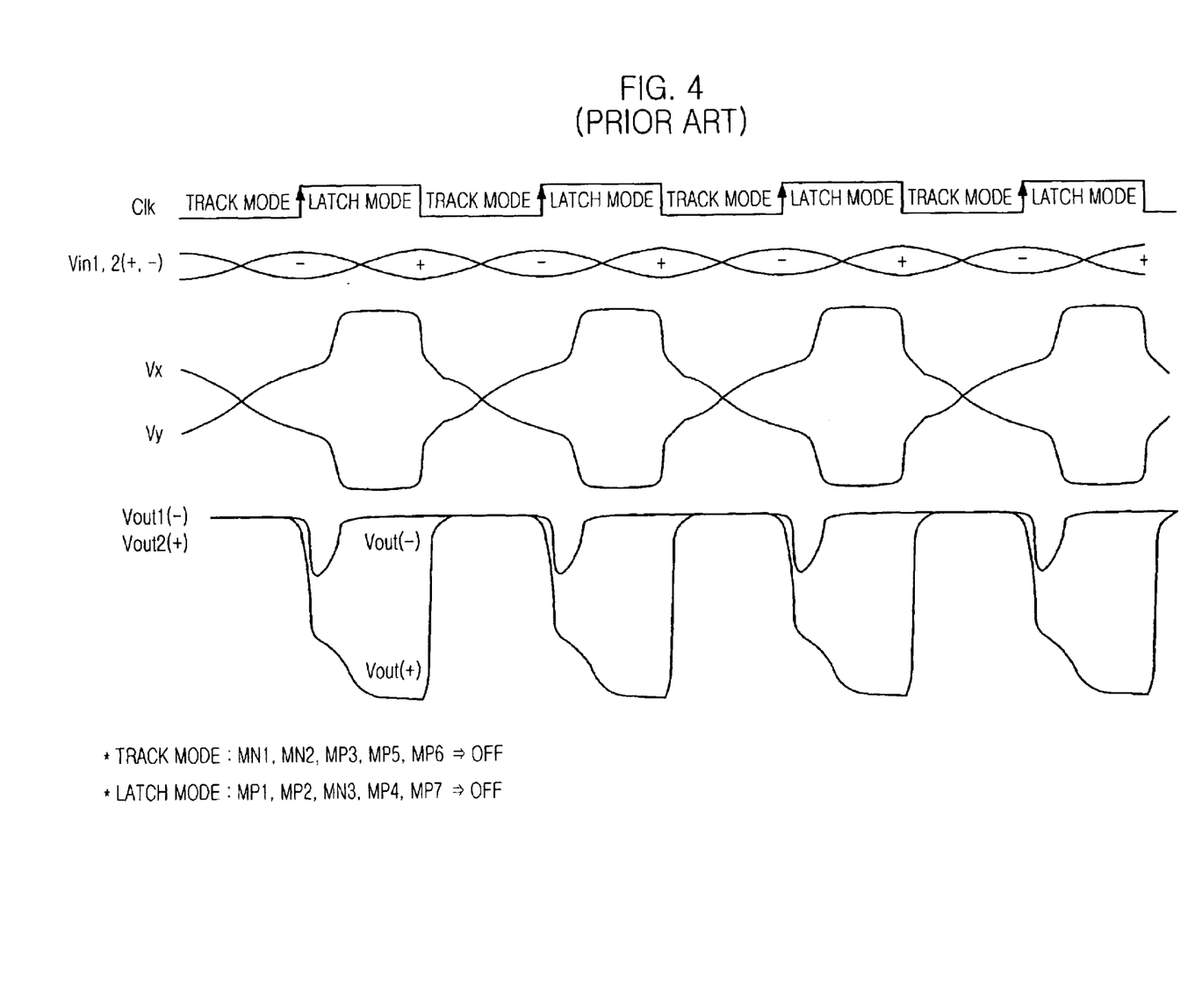
FIG. 4 is a timing chart illustrating an entire operation of the comparator shown in FIG. 2.

FIG. 3 illustrates an equivalent circuit of the track mode shown in FIGS. 3 and FIG. 4 is a timing chart illustrating an entire operation of the circuit shown in FIG. 2. The operation of the comparator is observed by referring to FIGS. 2, 3 and 4.

Herein, if the clock signal Clk is in a logic low state or a logic high state, the comparator is operated in the track mode or the latch mode, respectively.

First, in case that the clock signal Clk is in the logic low state, the MN1 and the MN2 are turned off, and the MP3 is also turned off. In a meantime, the MP4 and MP7 are turn on. Consequently, the Vout1 and Vout2 get identical to a voltage level at the VDD.

Accordingly, the latch operation is about to be performed by Vx and Vy respectively applied to the second node N2 and the first node N1 by two input signals Vin1 and Vin2. At this time, the MN3 is turned on and its turn-on resistance value becomes high. Consequently, the Vx and Vy approach to each other temporarily. Thereafter, the MN3 is operated in the track mode in which the Vx and Vy are amplified.

In the track mode, the comparator shown in FIG. 2 is commonly operated as a differential amplifier, and the analog signals Vin1 and Vin2 are amplified and tracked. At this time, a gain A of the analog signal Vin1 or Vin2 is obtained by below equation Eq. 1.

[First Mathematic Formula]

$$A = Gm1 \times Ron3 / (2 - Gm4 \times Ron3) \qquad \text{Eq. 1.}$$

Herein, 'Gm1' means a trans-conductance value for the MP1 and the 'Gm4' means the trans-conductance value for the MN4. In addition, the Ron3 means an impedance of the MN3.

Commonly, the differential amplifier is designed to have a result value 1 for 'Gm1×Ron3', that is, 'Gm1×Ron3=1'. However, if the result value of the 'Gm4×Ron3' becomes over 2, a denominator value of the first mathematic formula becomes negative. That means the circuit for the differential amplifier does not work as a normal amplifier. In this case, a positive feedback is commonly applied to the circuit and thereby, operating the circuit only in the latch mode. In short, voltage values of Vx and Vy are biased to be contrary to each other and the circuit does not get to response to the Vin1 and Vin2.

Accordingly, the circuit for the differential amplifier should be designed not to have the result value of 'Gm4× Ron3' over 2.

As shown in FIG. 4, each of Vx and Vy is amplified in the track mode. In addition, if the clock signal Clk is converted from the logic low state to the logic high state, all of the MP1, MP2, MN3, MP4 and MP7 are turned off and the MN3 is removed from the circuit as it is turned off.

As the MP3 is turned on, the current pass is formed from the VDD to the GND via the MP8 and MP3. At this time, PMOS transistors MP1, MP2 of the differential pair input terminal are turned off by the MP3 serving as the source follower.

Differential current from PMOS transistors MP1, MP2 of the differential pair input unit is generated by a voltage difference of the voltages Vx and Vy applied to the nodes N1 and N2.

As mentioned above, the differential voltage is amplified by a positive amplifier and the Vx and the Vy are diverged in a direction predetermined by an input voltage for a standard voltage.

The Vx and Vy are much more amplified and thereby, generating out-put voltages, that is, Vout(+) and Vout(−) in such wave forms shown in FIG. 4.

In addition, if the circuit shown in FIG. 3 is operated in a low voltage, a value of voltage Vgs3 applied between a gate and a source is reduced and thereby, increasing a value of Ron3. If Gm3 is decreased to reduce the value of 'Gm4×Ron3', the Vx and Vy are increased. Consequently, the Vgs3 of the MN3 is reduced and thereby, increasing the Ron3. Therefore, it is not easy to make the result value of 'Gm3×Ron5' become 1. Even though the Ron3 is reduced by increasing a width of the M5, the MN3 is in a turn-on condition slightly exceeding a threshold voltage. Accordingly, the MN3 gets close to a turn-off condition and a resistance value is rapidly increased in case that the threshold voltage of the MN3 is varied by a process change. Consequently, a possibility that 'Gm4×Ron3' is over 2 becomes high.

Furthermore, if a power voltage is varied, the value of the Ron4 is greatly varied because the MN3 is weakly turned on at a low power voltage. Accordingly, a stable operation of the circuit in accordance with the prior art can not be guaranteed.

SUMMARY OF THE INVENTION

It is, therefore, an object of the present invention to provide a comparator operated stably even at a low power voltage and preventing its property change caused by a process change.

In accordance with an aspect of the present invention, there is provided the comparator outputting one bit digital signal after comparing two analog input signals by alternately performing a track mode operation and a latch mode operation, wherein the operation of the track mode or the latch mode is decided by a clock signal having a constant period, including: a latching unit having the main/sub input terminal; a first switching transistor having the clock signal as a gate input and having one end coupled to main input terminal; a first load transistor diode-connected to the other end of the first switching transistor and a ground end; a second switching transistor having a gate receiving the clock signal as a gate input and one end coupled to the sub input terminal; and a second load transistor diode-connected to the second switching transistor and to the other end of the ground terminal.

BRIEF DESCRIPTION OF THE DRAWINGS

Other objects and aspects of the invention will become apparent from the following description of the embodiments with reference to the accompanying drawings, in which.

DETAILED DESCRIPTION OF THE PREFERRED EMBODIMENTS

Hereinafter, an inventive CMOS comparator outputting one bit digital signal after comparing two analog input signals by alternately performing a track mode operation and a latch mode operation will be described in detail referring to the accompanying drawings.

The present invention relates to the CMOS comparator using a low power voltage, for example, 1.8 V. Two groups of transistors are distinctly disposed to have a switch function and a resistor function, respectively. A stable gain without being affected by a voltage or current change or a process can be obtained by forming a ground terminal by using a current pass between two nodes.

Figure 5:
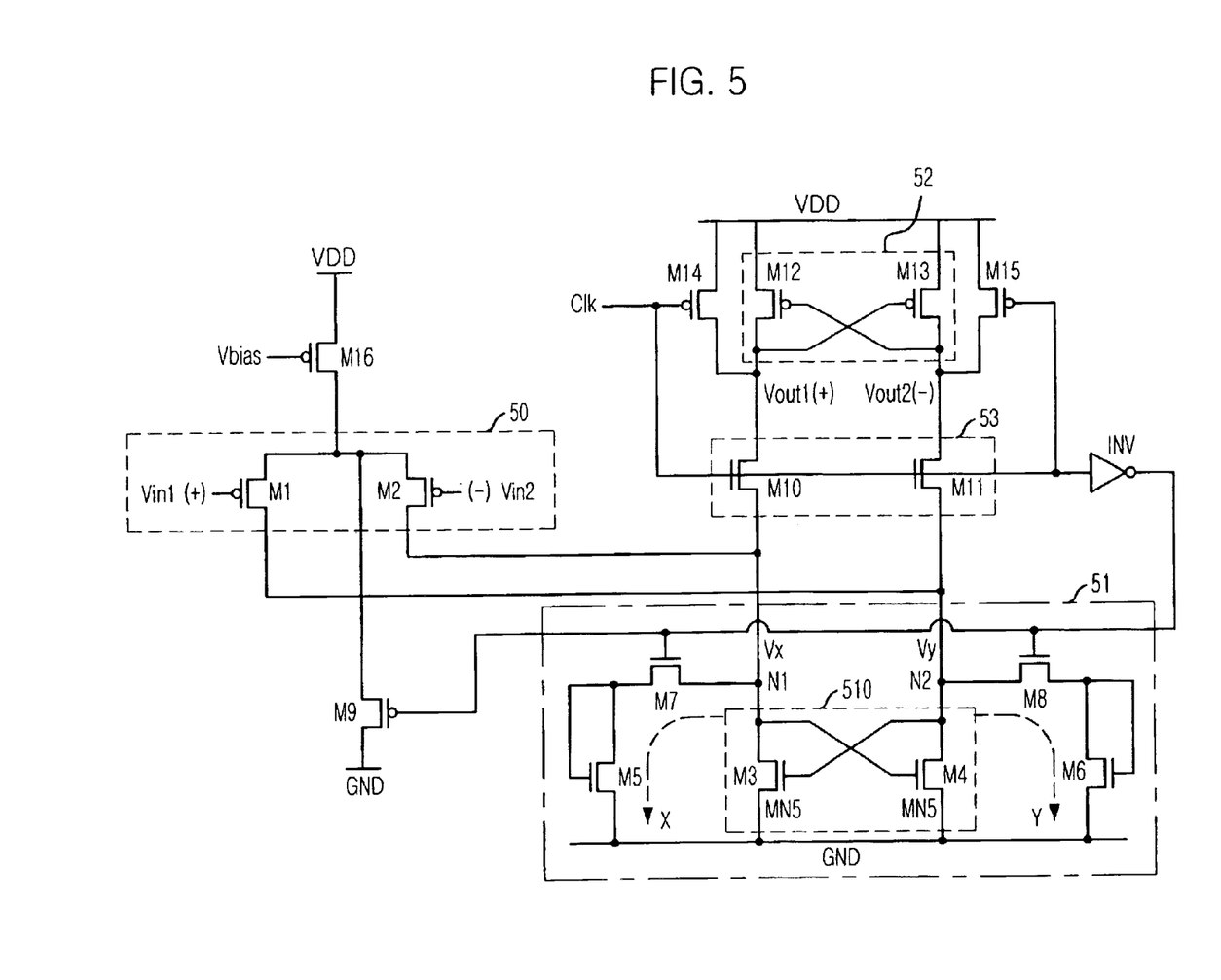
FIG. 5 is a detailed circuit diagram depicting a CMOS comparator used for an ADC, wherein the CMOS comparator is designed in accordance with an embodiment of the present invention.

FIG. 5 is a detailed circuit diagram of the CMOS comparator used for an analog to digital converter (ADC), wherein the CMOS comparator is designed in accordance with an preferred embodiment of the present invention.

Referring to FIG. 5, the CMOS comparator includes a differential input unit 50, a tracking/latching units 51 a second latching unit 52 and a switching unit. The differential input unit 50 is constituted with two PMOS transistors M1 and M2, wherein a first input signal Vin1 and a second input signal Vin2 are generated by the M1 and M2, respectively, and treated as a discrete input.

The tacking/latching units 51 receives the differential output at a main sub input terminals N1 and N2 from the differential input unit 50 and thereby, performing a tacking and latch operation. For this, tracking/latching units 51 are used. The differential input unit 50 in the track mode is operated as a load of the differential input unit 50 for the tacking operation and thereby, performing an operation of a differential amplifier.

The tacking/latching unit 51 includes a first latch unit 510 having a first node N1 as the main input terminal and a second node N2 as the sub input terminal, a first switching transistor M7 receiving a revered clock signal Clk by an inverter INV and having one end connected to the first node N1, a first load transistor M5 diode coupled to the other end of the first switching transistor M7 and coupled to the ground, a second switching transistor M8 receiving the reversed clock signal Clk by the inverter INV as a gate input and having one end coupled to the second node N2, and a second load transistor M6 diode coupled to the other end of the second switching transistor M8 and coupled to the ground.

The first latching unit 510 further includes a NMOS transistor M4 having a gate coupled to the first node N1 and a gate of a MMOS transistor M3 coupled to the second node N2.

Herein, a first current pass X between the first node N1 and the ground terminal GND is formed by the first switching transistor M7 and the first load transistor M5, and a second current pass Y between the second node N2 and the ground terminal GND is formed by the second switching transistor M8 and the second load transistor M6. Consequently, the tracking operation is performed.

An explanation for the tracking operation will be described later.

In addition, the first load transistor M5 and the second load transistor M6 need to be large enough to neglect turn-on resistances of the first switching transistor M7 and the second switching transistor M8, respectively. At this time, size of the first load transistor M5 should be identical to that of the second load transistor M6 and also, size of the first switching transistor M7 should be identical to that of the second transistor M8.

In addition, a second latching unit 52 resets a prior voltage level of output terminals Vout1 and Vout2 to the voltage level of a drain voltage terminal VDD in the track mode and generates output of the tracking/latching units 51 through output terminals Vout1 and Vout2 by latching the output of the tracking/latching units 51 in the latch mode.

The second latching unit 52 responding to the clock signal Clk includes a main output terminal Vout1, sub output terminal Vout2 and two PMOS 12 and 13. The main output terminal and the sub output terminal are cross coupled to gates of two PMOS transistors.

A switching unit 53 is formed in between the second latching unit 52 and the tracking/latching unit 51 for connecting or disconnecting the second latching unit 52 and the tracking/latching unit 51 in response to the clock signal Clk.

In addition, a fifth and sixth switching transistor are operated as a switch in order to reset output terminals Vout1 and Vout2 by using the second latch unit 52 when the latch mode is transformed to the track mode according to the clock signal Clk by receiving the clock signal Clk into gates of transistor M14 and M15, and forming the source-drain path between the power voltage terminal VDD and the output terminals Vout 1 and Vout 2.

In addition, a PMOS transistor M9 is formed to serve as a source-follower which forms a current pass between the drain voltage terminal VDD and the ground terminal GND via a bias transistor M16. Herein, the PMOS transistor is turned on in the latch mode and performs the above mentioned operation. Furthermore, the differential input unit 50 is turned off in the latch mode thereby.

Figure 6:
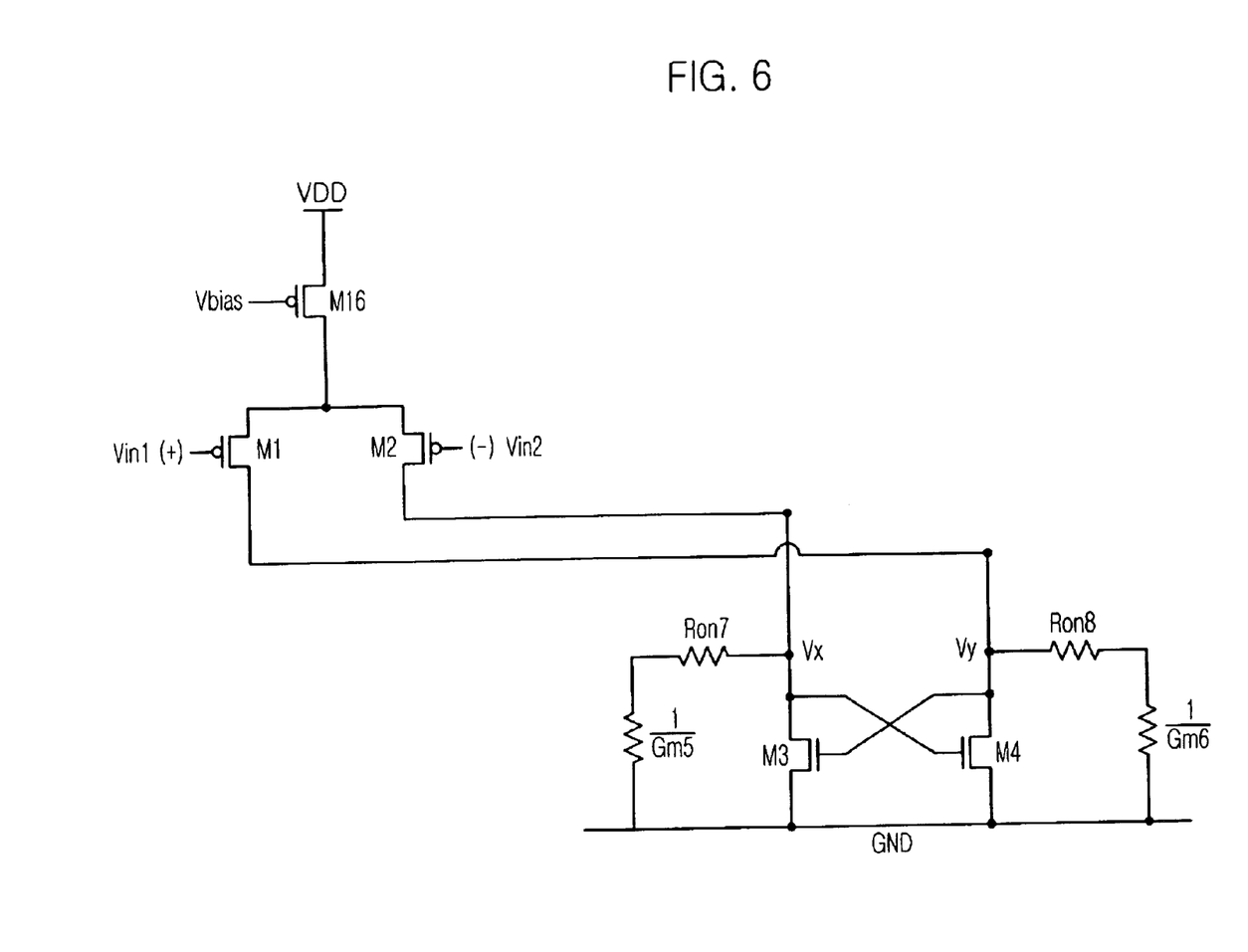
FIG. 6 is an equivalent circuit diagram of the CMOS comparator operated in a track mode as shown in FIG. 5.
Figure 7:
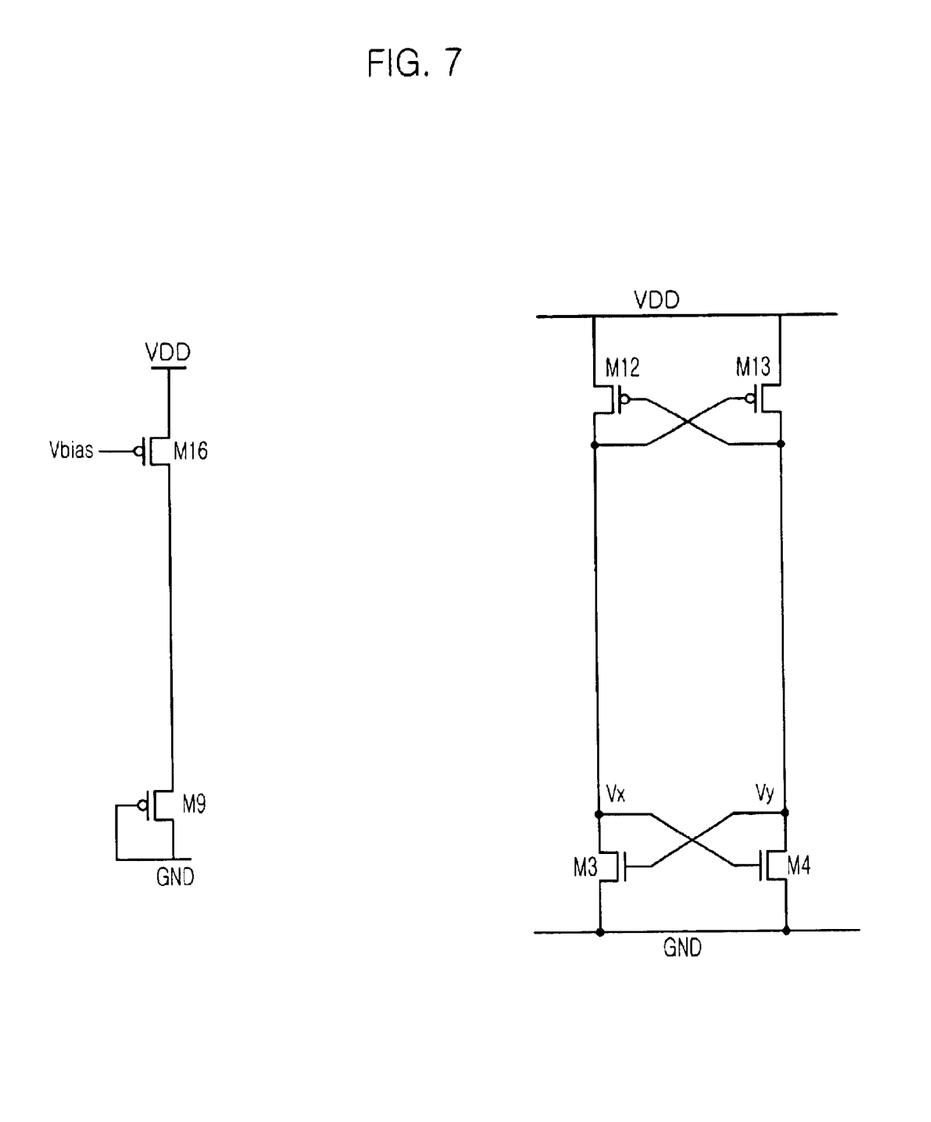
FIG. 7 is an equivalent circuit diagram of the CMOS comparator operated in a latch mode as shown in FIG. 5.
Figure 8:
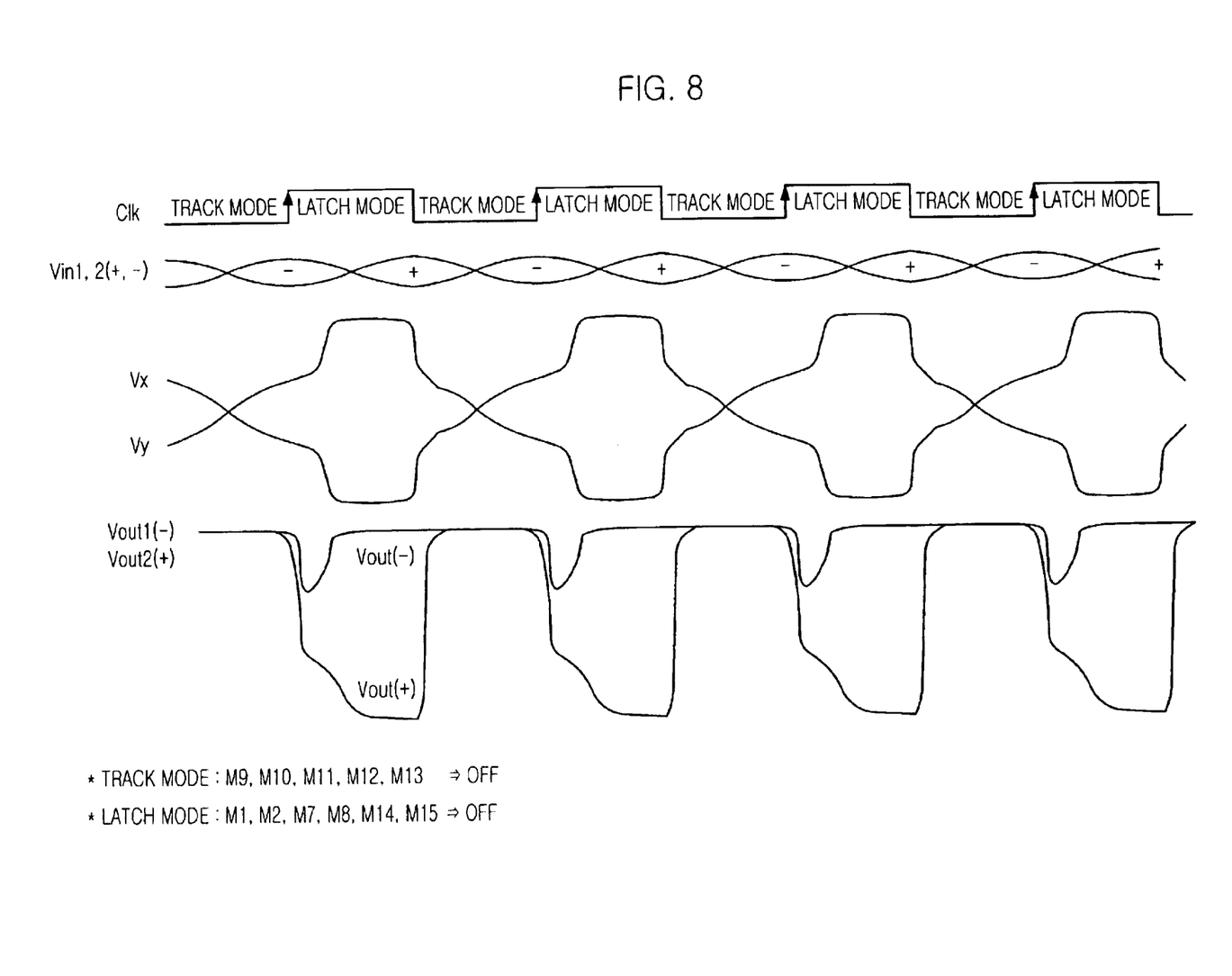
FIG. 8 is a timing chart illustrating an entire operation of the CMOS comparator shown in FIG. 5.

FIG. 6 illustrates an equivalent circuit of the detailed circuit of the CMOS comparator shown in FIG. 5. FIG. 7 illustrates the equivalent circuit in the latch mode. FIG. 8 is a timing chart showing whole operation of the CMOS comparator shown in FIG. 5.

Hereafter, the operation of the comparator in accordance will be described referring to FIG. 5 or FIG. 8, and the abbreviation of each transistor is used for description simplicity.

Herein, it is supposed that the comparator is operated in the track mode when the clock signal Clk is in a logic low state and the comparator is operated in the latch mode when the clock signal Clk is in a logic high state.

First, if the clock signal Clk becomes the logic low state, M1 and M2 are turned off and M9 is also turned off. The other hand, M14 and M15 are turned on. As a result, Vout1 and Vout2 become identical to a voltage level of the drain voltage terminal VDD.

Accordingly, a voltage Vy applied to the second node N2 and another voltage Vx applied to the first node N1 are latched by the input signals Vin1 and Vin2, respectively. At this time, M7 and M8 are turned on. Herein, a current pass to the ground terminal GND is formed by transistors M5 and M6 respectively diode-connected with the M7 and M8.

Consequently, it is operated as the track mode and Vx and Vy are located and amplified.

In such track mode, the comparator illustrated in FIG. 5 is operated as a common differential amplifier, and amplifies and tracks analog input signals of Vin1 and Vin2. At this time, a direct current DC gain A of the amplifier is calculated by belowe equation Eq. 2.

$$A = Gm1/(Gm5 - Gm3) \qquad \text{Eq. 2}$$

Herein, Gm1, Gm5 and Gm3 are trans-conductance of M1, M5, and M3, respectively.

Referring to the FIG. 6 and the above expressed the mathematic formula 2, the turn-on resistance Ron7 of M7 is neglected because the Ron7 is series-connected with 1/Gm5 and much lower than 1/Gm5. In addition, output impedance values of M5 and M3, that is, Ron5 and Ron3 are also neglected because the Ron5 and Ron3 are much higher than 1/Gm5 even though parallel-connected to 1/Gm5.

According to the Eq 2, the circuit of the comparator in accordance with the present invention should be devised to keep a positive value of the denominator 'Gm5−Gm3'. Generally, the positive value is maintained by increasing the value of Gm5. Accordingly, the gain value becomes stable. In addition, Vx and Vy are lowered if the value of Gm5 is increased. Consequently, the turn-on resistance of M7 is decreased. Herein, Gm5 and Gm3 are kept to have a constant value regardless of changes of a power voltage and a threshold voltage. However, only one factor, that is, a bias current merely affects the values of Gm5 and Gm3.

In case that the value of Gm3 is a little lower than that of Gm5, it is possible to increase the gain of the amplifier much more and thereby, improving a resolution of the comparator.

Gm3 and Gm5 can be constantly maintained constant by adjusting a transistor rate (W/L) regardless of the change of manufacturing process steps and a power voltage and thereby, guaranteeing a stable operation of the comparator.

As shown in FIG. 8, each of Vx and Vy is amplified in the track mode, and all of M1, M2, M7, M8, M14, and M15 are turned off when the clock signal Clk in the logic low state is converted to that in the logic high state.

Accordingly, M7 and M8 are removed from a real circuit.

A current pass is formed from the VDD to M9 via M16 as M9 is turned on, and M1 and M2 are turned off.

A differential current from the PMOS transistors M1 and M2 of the differential input unit 50 is generated by a difference between Vx and Vy. Herein, Vx is the voltage of N1 and Vy is the voltage of N2. Such differential current is amplified by a positive amplifier. Furthermore, Vx and Vy are diverged in predetermined directions by an input voltage for a standard voltage. Vx and Vy are much more amplified. Consequently, Output voltages Vout1(+) and Vout2(−) are generated in a wave shape shown in FIG. 8.

More specifically, M1 and M2 serve as a pre-amplifier amplifying the input signal after receiving the input signal when the comparator is in the track mode. At this time, M3, M4, M5 and M6 receive the input signal. The gain of the amplified signal is 'Vx–Vy'.

In the track mode, M10 and M11 are turned off, and Vx and Vy are not affected by M12, M13, M14 and M15. M14 and M15 are turned on. As a result, Vout1 and Vout2 become identical to the drain voltage terminal VDD and consequently, a memory effect deciding voltage polarity when a prior latch state is converted to a next latch mode is eliminated. In short, output latch state becomes reset.

When the comparator is operated in the latch mode, M10 and M11 are turned on and M14 and M15 are turned off. In addition, M7 and M8 are turned off as shown in FIG. 7 and operated as a typical latch circuit. At this time, a gate voltage of M9 is reduced to the voltage level of the ground terminal GND. Consequently, electrical current does not flow to M1 and M2, and Vin1 and Vin3 do not affect the first and second latch units 510 52 anymore. Furthermore, the node having a relatively high voltage obtains the voltage level identical to the drain voltage terminal VDD through a positive feedback of the first and the second latch units 510 and 52. At this time, an initial state of a moment of starting the latch mode by Vx and Vy is kept. Contrarily, the node having a relatively low voltage obtains the voltage level of the ground terminal GND and digital signals are generated. FIG. 8 illustrates real output waveforms of such Vout1 and Vout2.

As mentioned above, the present invention can prevent variation of characteristic according to change of power voltage or variation of process by designing a comparator having stable gain of amplifier not to be affected by threshold voltage and power voltage of transistor in tracking mode.

Also, the present invention can be implemented not only device comparing two analog signals.

Furthermore, by designing a gain of comparator not to be affected by process variation and power voltage change in order to have independent characteristic, the present invention can increased efficiency of manufacturing comparators.

Although the preferred embodiment of the invention have been disclosed for illustrative purposes, those skilled in the art will appreciate that various modifications, additions and substitutions are possible, without departing from the scope and spirit of the invention as disclosed in the accompanying claims.

What is claimed is:

1. A comparator outputting one bit digital signal after comparing two analog input signals by alternately performing a track mode operation and a latch mode operation decided according to a clock signal, the comparator comprising:

a differential input unit for receiving the two analog input signals and outputting a different output;

a tracking/latching unit for receiving the differential output through a main input terminal and a sub input terminal of the tracking/latching unit in order to perform the track mode operation and the latch mode operation according to the clock signal; and a first latching unit for latching and outputting an output of the tracking/latching unit;

wherein each of the main input terminal and the sub input terminal has a different current pass for having a constant gain of the comparator during the track mode operation.

2. The comparator as recited in claim 1, wherein the tracking/latching unit includes:

a second latching unit having the main input terminal and the sub input terminal;

a first switching transistor having the clock signal as a gate input and having one end coupled to the main input terminal;

a first load transistor which is diode-connected between the other end of the first switching transistor and ground;

a second switching transistor having a gate receiving the clock signal as a gate input and one end coupled to the sub input terminal; and a second load transistor which is diode-connected between the other end of the second switching transistor and ground.

3. The comparator as recited in claim 2, wherein the first load transistor and the second load transistor are large enough to neglect the first switching transistor and the second switching transistor, respectively.

4. The comparator as recited in claim 3, wherein size of the first switching transistor is identical to that of the second switching transistor and size of the first load transistor is identical to that of the second switching transistor.

5. The comparator as recited in claim 2, wherein the second latching unit includes a first transistor and a second transistor whose gates are cross-connected to the main input terminal and the sub input terminal, respectively.

6. The comparator as recited in claim 1, wherein the comparator further includes a switching unit in order to connect or disconnect the first latching unit with the tracking/latching unit in response to the clock signal.

7. The comparator as recited in claim 6, wherein the switching unit includes a third switching transistor and a fourth switching transistor whose gates receive the clock signal, wherein the third switching transistor is connected between the first latching unit and the main input terminal and the fourth switching transistor is connected between the first latching unit and the sub input terminal.

* * * * *